US009258642B2

(12) United States Patent
Nissila et al.

(10) Patent No.: US 9,258,642 B2
(45) Date of Patent: Feb. 9, 2016

(54) AUDIO-OPTICAL ARRANGEMENT, ACCESSORY, EARPIECE UNIT AND AUDIO DEVICE

(75) Inventors: Juuso Nissila, Ii (FI); Antti Aunio, Oulu (FI); Juha Tiikkainen, Liminka (FI)

(73) Assignee: Valkee OY (FI)

( * ) Notice: Subject to any disclaimer, the term of this patent is extended or adjusted under 35 U.S.C. 154(b) by 479 days.

(21) Appl. No.: 13/990,610

(22) PCT Filed: Dec. 17, 2010

(86) PCT No.: PCT/FI2010/051058
§ 371 (c)(1),
(2), (4) Date: Jul. 29, 2013

(87) PCT Pub. No.: WO2012/080559
PCT Pub. Date: Jun. 21, 2012

(65) Prior Publication Data
US 2013/0301851 A1    Nov. 14, 2013

(51) Int. Cl.
*H04R 3/00*        (2006.01)
*A61M 21/00*       (2006.01)
*A61M 21/02*       (2006.01)
*A61N 5/06*        (2006.01)
*H04R 1/10*        (2006.01)
*H04R 23/00*       (2006.01)

(52) U.S. Cl.
CPC .................. *H04R 3/00* (2013.01); *A61M 21/00* (2013.01); *A61M 21/02* (2013.01); *A61N 5/0618* (2013.01); *H04R 1/1091* (2013.01); *H04R 23/008* (2013.01); *A61M 2021/0027* (2013.01); *A61M 2205/051* (2013.01); *A61M 2210/0662* (2013.01); *A61N 5/0622* (2013.01); *A61N 2005/063* (2013.01); *A61N 2005/065* (2013.01); *A61N 2005/0647* (2013.01)

(58) Field of Classification Search
None
See application file for complete search history.

(56) References Cited

U.S. PATENT DOCUMENTS

| | | | |
|---|---|---|---|
| 6,078,829 A | 6/2000 | Uchida et al. | |
| 6,080,110 A * | 6/2000 | Thorgersen | 600/500 |
| 2003/0233051 A1 | 12/2003 | Verjus et al. | |
| 2005/0137656 A1 | 6/2005 | Malak | |
| 2005/0209516 A1 | 9/2005 | Fraden | |
| 2006/0271130 A1 | 11/2006 | Mayer-Gindner et al. | |
| 2008/0046042 A1 | 2/2008 | Branch | |
| 2010/0042188 A1 | 2/2010 | Nissila et al. | |
| 2010/0217102 A1 * | 8/2010 | LeBoeuf et al. | 600/310 |

FOREIGN PATENT DOCUMENTS

| | | |
|---|---|---|
| CN | 101524289 | 9/2009 |
| JP | 4257294 | 4/2009 |

OTHER PUBLICATIONS

Chinese Office Acton dated Mar. 3, 2015, 9 pages.

* cited by examiner

*Primary Examiner* — Brenda Bernardi
(74) *Attorney, Agent, or Firm* — Tarolli, Sundheim, Covell & Tummino LLP (57) ABSTRACT

There is provided an arrangement, an accessory, an audio device, and at least one earpiece unit. The accessory is suitable for an audio device capable of providing an electrical audio signal. The accessory comprises first and second signal conveyers for conveying electrical audio signal driving audio transducers and electrical optic signal driving optical radiation sources, respectively. The audio transducers and the optical radiation sources are located in the earpiece unit.

23 Claims, 4 Drawing Sheets

AUDIO-OPTICAL ARRANGEMENT, ACCESSORY, EARPIECE UNIT AND AUDIO DEVICE

FIELD

The invention relates generally to an accessory for devices capable of providing audio signal to a user.

BACKGROUND

It is common for people to listen to music with a music player via ear plugs. Listening to music is a one way of relaxing oneself and to improve the mental condition of the listener, for example. Moreover, people are nowadays applying various other methods to improve the physical or mental condition as well. One may seek the improvement from traditional means, such as exercise or sleep, while another relies in more technical means, such as receiving optical radiation from an optical treatment device. However, it may happen that these methods are mutually excluding.

BRIEF DESCRIPTION OF THE INVENTION

Embodiments of the invention seek to enable receiving optical treatment and listening to music simultaneously.

Embodiments of the invention are defined in the dependent claims.

LIST OF DRAWINGS

In the following, the invention will be described in greater detail with reference to the embodiments and the accompanying drawings, in which.

DESCRIPTION OF EMBODIMENTS

The following embodiments are exemplary. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments.

Figure 1:
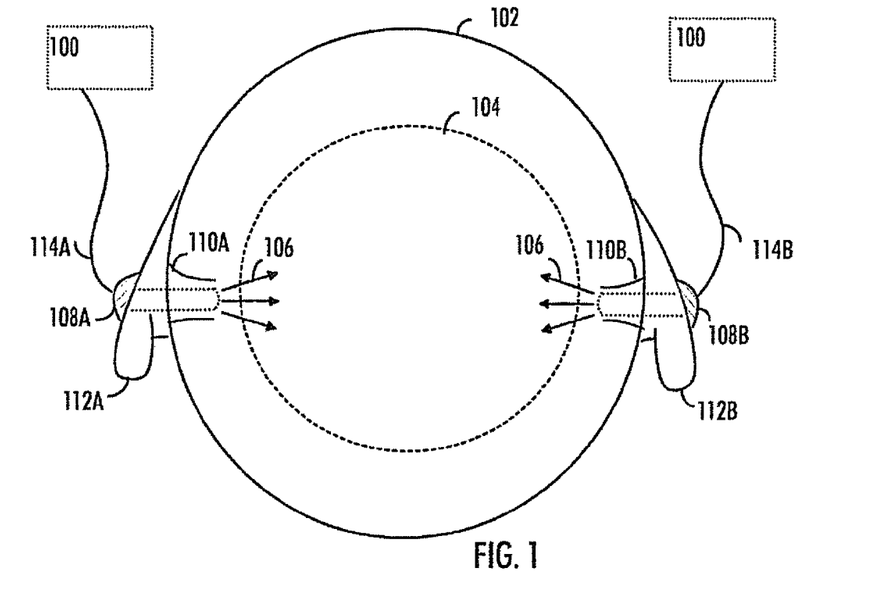
FIG. 1 presents a portable device for providing optical treatment according to an embodiment.

Let us first discuss what optical treatment is and how it can be provided with reference to FIG. 1. Human nerve tissue includes regions that may be stimulated by optical radiation directed at the regions. Stimulation may have a metabolic and/or nervous response, which may appear as a change in alertness, diurnal (circadian) rhythm and in concentrations of several hormones and brain transmitters. The optical radiation may originate from nature or the optical radiation may have an artificial origin. A lack in the amount of the optical radiation energy (i.e. light) may cause a seasonal affective disorder (SAD) or depression in humans, for example.

It may thus be advisable to use artificial optical radiation when natural light is not sufficient in order to prevent undesired physiological effects. This type of artificial light may be generated by bright light therapy devices installed in homes or workplaces, for instance. However, the optical treatment may also be obtained with a portable electronic device (PED). The portable electronic device may comprise radiation means for directing optical radiation energy non-invasively at a tissue of the user 102 in order to stimulate the user's 102 tissue. The PED may comprise a central unit 100 of the PED, radiation members 108A, 108B for emitting optical radiation and wires 114A and 114B for connecting the central unit 100 and the radiation members 108A, 108B, respectively. The wires 114A and 114B may be used in conveying instructions to the radiation members 108A and 108B and/or to convey the optical energy to the radiation members 108A, 108B, respectively.

In an embodiment of FIG. 1, the user 102 is using the PED such that the optical radiation 106 is directed through an audio auditory canal 110A and 110B of the user 102 of the portable electronic device. The Figure shows the user's 102 head from top view. The audio auditory canals 110A and 110B may form part of the user's 102 ears 112A and 112B. The radiation members 108A, 108B direct optical radiation 106 at the user's 102 ear auditory canals 110A and 110B, respectively, which conveys the transmitted optical radiation energy 106 to the intracranial nerve tissue 104. In that case, the intracranial nerve tissue 104 is subjected to a treatment that has a response in the intracranial nerve tissue of a brain 104. In this context, the terms "optical radiation" and "optical radiation energy" are equivalent concepts, and the same reference number 106 is used to denote both. Optical radiation 106 typically comprises the wavelengths of infrared radiation, visible light and ultraviolet radiation.

Thus, the optical radiation energy 106 is received in the radiation-sensitive nerve tissue, which is stimulated by the optical radiation energy 106. For example, the intracranial nerve tissue of the brain 104 responsive to optical radiation energy 108 comprises, for example, cerebrum, cerebellum, vestibular organs, auditory organs, organs of smell, bulbus, a pineal body, also known as a pineal gland, and/or regions of autonomic regulation. The response may be based on a change in the concentration of melatonin hormone caused by the optical radiation 106, for example.

In an embodiment, the intracranial nerve tissue responsive to optical radiation 108 comprises a retina, whose ganglia cells may also sense light arriving from behind. Typically, the visual perception of ganglia cells is independent of seeing and not involved therein. Ganglia cells are in particular specialized for diffused light and their photosensitive pigment is melanopsin protein. When subjected to light, ganglia cells signal suprachiasmatic nucleus, which is the primary agent responsible for the circadian rhythm.

In an embodiment, the intracranial nerve tissue 104 responsive to optical radiation energy 108 comprises a suprachiasmatic nucleus (SCN) which regulates the pineal body, which back-regulates the SCN by excreting melatonin. The suprachiasmatic nucleus may also be responsible for controlling the circadian rhythms.

It should be noted that the above-mentioned intracranial nerve tissues of brain 104 that is responsive to optical radiation energy 106 is only an example. Some of the light also affects through other means, for example through neuroendocrinology of diurnal rhythm. Intracranial nerve tissues, also in the cranial region, have several non-specific responses to optical radiation energy 106 and the temperature increase caused by the optical radiation energy 106. Such responses include increase in the metabolism of tissues and changes in the immune response.

The optical radiation 106 may affect the user 102 in many ways. The optical treatment that comprises illuminating an optically sensitive tissue of the user 102 with optical radiation energy 106 may improve physiological condition of the user 102. The effects which may be obtained with the optical treatment include but is not limited to the following: changes of diurnal rhythm, treatment of jetlag, treatment of sleep irregularity caused by shift work, exceptional change of sleep rhythm, treatment of seasonal affective disorder (SAD) and other affective syndromes, temporary increase of performance, waking up, alleviation of stress symptoms, nervous disorders caused by decreased light sensitivity of brain, improvement of plasticity of nerve system, and treatment of sexual insufficiency. It may further have effect in preventing an infection, treatment of certain diseases, such as the Parkinson's disease, treatment of depression, and treatment of depressive symptoms, for example. For example, when a person 102 is suffering from a bipolar disorder or manic-depressive disorder, which is also referred to as bipolar affective disorder or manic depression, the person 102 may treat the disease with certain doses of illumination directed to photosensitive tissues of the person, such as the intracranial nerve tissue. The person 102 may notice that the depression is relieved with appropriate doses of the optical radiation 106.

Other ways to improve one's physiological condition may comprise listening to music. Of course music may be listened for other purposes as well. Music may be listened with an audio player. The audio player may be a portable audio player which the user 102 may carry with him/her. The audio player may in that case be responsible for conveying electrical audio signal to a speaker (a transducer) located at an ear-plug. The ear-plug may be put on by the user 102 in his/her ears so that the audio signals produced by the speaker are heard by the user 102. However, this may not be possible when the user 102 is at that moment enjoying his optical treatment dosage as discussed with reference to FIG. 1.

Figure 2A:
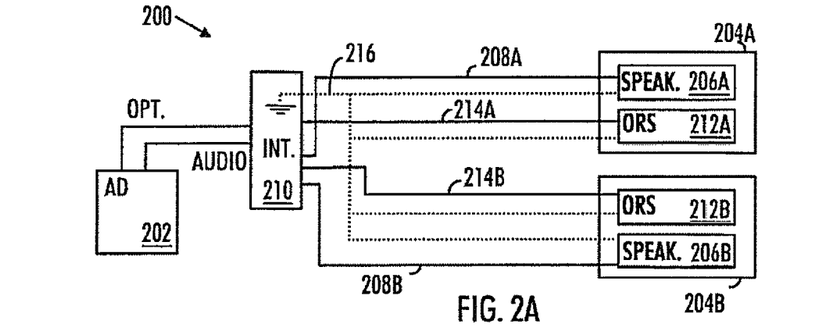
FIGS. 2A and 2B show an accessory according to an embodiment.
Figure 2B:
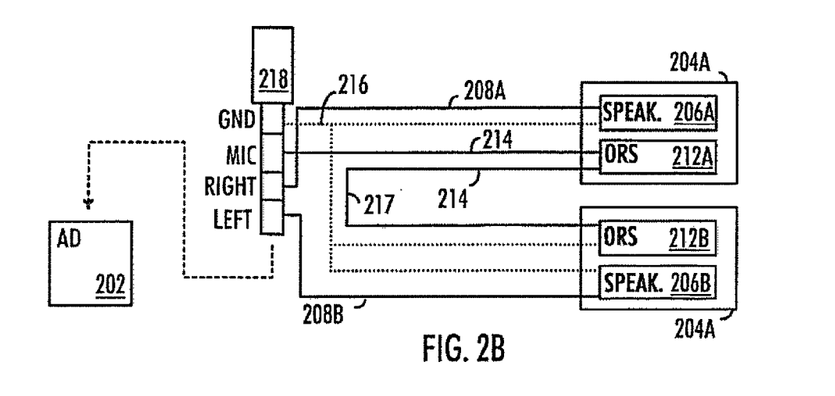

For this reason there is provided an accessory 200 for an audio device (AD) 202 capable of providing electrical audio signal as shown in FIGS. 2A and 2B. The audio device may be a mobile phone, an MP3 player, a palm computer, a personal computer, etc.

In an embodiment the accessory 200 comprises at least one earpiece unit 204A, 204B, each comprising an audio transducer 206A, 206B configured to provide sound to a user 102. The earpiece unit may be an earplug, for example. The user 102 may put the earpiece unit 204A, 204B on his/her ear 112A, 112B, respectively. The audio transducer 206A, 206B may be a loud speaker, for example.

The accessory 200 may further comprise a first signal conveyer 208A, 208B for conveying an electrical audio signal to each audio transducer 206A, 206B in order to drive the audio transducer 206A, 206B. By driving it is meant controlling and powering the destination. The transducer 206A, 206B may convert the electrical audio signal into sound. The loud speaker moves in accordance with the variations of an electrical audio signal and causes sound waves to propagate through a medium such as air or water. The first signal conveyer 208A, 208B may comprise at least one wire, for example. In an embodiment, the first signal conveyer 208A, 208B may comprise one wire for each earpiece unit 204A, 204B, respectively, in order to generate a right audio channel and a left audio channel.

The accessory 200 may further comprise a communication interface 210 for receiving the electrical audio signal from the audio device 202 and for outputting the electrical audio signal to the first signal conveyer 208A, 208B. In other words, as the audio device 202 outputs the electrical audio signal as shown with the "AUDIO" connection in FIG. 2A, the communication interface 210 may forward the electrical audio signal to the earpiece unit 204A, 204B and to the audio transducer 206A, 206B, respectively, in order to provide music to the user 102. The audio device 202 may feed different audio signal for each loud speaker 206A, 206B, i.e. for each earpiece unit 204A, 204B, or the electrical audio signal fed from the audio device 202 may be common to each audio transducer 206A, 206B. The choice may depend on is stereo audio required or not, or whether the user 102 desires to listen one type of audio track from one loud speaker and other audio track from another loud speaker, for example.

Each earpiece unit 204A, 204B may further comprise at least one optical radiation source (ORS) 212A, 212B. The at least one optical radiation source 212A, 212B may provide optical radiation to the user 102, wherein the optical radiation is for illuminating an optically sensitive tissue of the user 102. Thus, the ORS 212A, 212B are used for providing optical treatment to the user. The at least one optical radiation source 212A, 212B may comprise at least one light emitting diode, an optical fiber, for example. In this sense, the at least one optical radiation source 212A, 212B is similar to the radiation members 108A, 108B of FIG. 1. However, as said earlier, now the earpiece unit 204A, 204B is also equipped with audio transducers 206A, 206B.

The accessory may further comprise a second signal conveyer 214A, 214B configured to convey at least one electrical optic signal to the at least one optical radiation source 212A, 212B in order to drive the at least one optical radiation source 212A, 212B. By driving it is meant controlling and powering the destination. The electrical optic signal may be an electrical signal that is used to feed the optical radiation source 212A, 212B, that is, it may be an electrical power signal. The word "optical" is used to distinct from the electrical audio signal, which is also an electrical signal feeding the audio transducer 206A, 206B.

The sound generated by the audio transducer 206A, 206B enables the person to listen to music or audio books, for example. In an embodiment, the sound comprises audio instructions on how to use the optical treatment. The instructions may comprise information on how long and at what intensity the optical radiation is to be received. This is advantageous so that the user receives information on the optical treatment (for example an audio guide on how to receive the optical treatment) when the user puts the ear plugs on his/her ears. In an embodiment, the sound comprises audio therapy related sounds. This is advantageous in order for the user to enjoy separate relaxation means, the optical radiation and the audio therapy.

Further, the audio transducer 206A, 206B may provide audio signals to the user, which audio signals represent audio signals heard in the surroundings of the user. In this case, there may be a microphone present in the accessory or in the audio device, and the audio transducers 206A, 206B may provide those audio signals which are received by the microphone to the user. The microphone and the audio transducers 206A, 206B may in this case be logically connected to each other.

The communication interface 210 may further be configured to output the at least one electrical optic signal to the second signal conveyer 214A, 214B. This way the electrical optic signal may be used in controlling the at least one optical radiation source 212A, 212B. The second signal conveyer 214A, 214B may comprise at least one wire, for example. In an embodiment, the second signal conveyer 214A, 214B may comprise one wire for each earpiece unit 204A, 204B, respectively, in order to provide control signal and, thus, power to the at least one optical radiation source 212A located in the right earpiece unit 204A and to the at least one optical radiation source 212B located in the left earpiece unit 204B.

It is to be noted that the second signal conveyer 214A, 214B is different from the first signal conveyer 208A, 208B. This is advantageous in order to enable the user 102 to simultaneously listen to the music and to receive optical radiation as the optical treatment. The different first and second signal conveyer allows separate but simultaneous controlling of the at least one optical radiation source 212A, 212B and the audio transducers 206A, 206B. Thus, music listening need not prevent simultaneous optical treatment. Having both, the at least one optical radiation source 212A and the audio transducer 206A, connected to the same signal conveyer would prevent simultaneous listening and optical treatment. Moreover, the at least one optical radiation source 212A would suffer from decreased power input due to the fact that the transducer 206A would eat part of the power fed to the optical radiation source 212A, or vice versa.

The electrical optic signal driving the at least one optical radiation source 212A, 212B may be used in determining the duration of the illumination, i.e. how long the at least one optical radiation source 212A, 212B emits optical radiation, the intensity of the illumination, the frequency of the illumination, etc. The duration of the illumination may be determined by feeding the electrical optic signal and, thus, power to the at least one optical radiation source 212A, 212B only during a predetermined time period. Similarly, the frequency of emitting the radiation may be determined by providing the electrical optic signal to the at least one optical radiation source 212A, 212B according to predetermined time intervals. The intensity of the optical radiation emitted by the at least one optical radiation source 212A, 212B may be determined by controlling the current/voltage of the electrical optic signal fed to the at least one optical radiation source 212A, 212B.

In the embodiment of FIG. 2A, the audio device 202 is responsible of providing the electrical optic signal driving the at least one optical radiation sources 212A, 212B. This is shown with the "OPT" connection from the audio device 202 to the communication interface 210. Thus, the power needed to operate the at least one optical radiation source 212A, 212B comes from the audio device. The electrical optic signal thus provides control capabilities and power to the at least one optical radiation source 212A, 212B. This is advantageous in that no additional power source is needed in the accessory 200.

In an embodiment, the communication interface may further comprise a single reference signal point to each audio transducer and each optical radiation source. This type of reference point may be the ground, for example, as is shown in FIGS. 2A and 2B with dotted line 216.

In the embodiment of FIG. 2B, the communication interface 210 is an audio jack 218, such as the 3.5 mm four-contact audio jack. The contacts ("LEFT", "RIGHT", "MIC", and "GND") may be used as follows: one contact ("RIGHT") is for receiving and outputting the electrical audio signal from the audio device 202 to the first signal conveyer 208A in order to generate a right audio channel, one contact ("LEFT") is for receiving and outputting the electrical audio signal from the audio device 202 to the first signal conveyer 208B in order to generate a left audio channel, one contact ("GND") is for providing the common reference point 216, and one contact ("MIC") is for receiving and outputting the electrical optic signal from the audio device 202 to the second signal conveyer 214 in order to control the at least one optical radiation source 212A, 212B. Therefore, instead of applying the "MIC" contact as the input for signals from a microphone, the "MIC" contact (pin) is used for feeding the electrical optic signal controlling and powering the at least one optical radiation source 212A, 212B.

In an embodiment, the second signal conveyer 214 is a single conducting wire common to each optical radiation source 212A, 212B. In this case, the communication interface 218 is configured to output a single electrical optic signal via the "MIC" contact, such that each optical radiation source 212A, 212B obtains the same electrical optic signal via the wire 214. It can be seen from FIG. 2B, that the wire 214 first travels to the first earpiece unit 204A and then continues to the second earpiece unit 204B before being brought into contact with the grounding point 216. The midpoint 217 of the loop of the wire 214 between the two earpiece units 204A, 204B may be outside the communication interface 218 or inside the communication interface 218. The advantage of having the midpoint 217 outside the communication interface 218 is that there is no need for extra apertures in the communication interface 218. The advantage of having the midpoint 217 inside the communication interface 218 is that the wire 214 does not so easily get mixed or entangled with the first signal conveyer 208A, 208B and/or with the rest of the second signal conveyer 214.

In an embodiment, as shown on FIG. 2A, the communication interface 210 may be configured to output a plurality of electrical optic signals, each electrical optic signal controlling a specific optical radiation source 212A, 212B. The electrical optic signal travelling via the second signal conveyer 214A may control the optical radiation source 212A, while another electrical optic signal travelling via the second signal conveyer 214B controls the optical radiation source 212B. This is advantageous so that the user 102 may determine separately for each optical radiation source 212A, 212B when and at what intensity the at least one optical radiation source 212A, 212B emits the optical radiation to the user 102.

When each or at least one earpiece unit 204A, 204B comprises more than one optical radiation source, the different electrical optic signals may be used to control each optical radiation source within a single earpiece unit 204A, 204B separately. This is advantageous when the user 102 requires the optical radiation to be oriented in a certain direction. The orientation of the optical radiation may be used to affect only a certain part of the nerve tissue or only certain optically sensitive cells. For example, when several optical radiation sources are located in one earpiece unit in the periphery of a circle, the user 102 may control the optical radiation sources so that only some of the several sources emit light. This may cause the optical radiation to propagate only to a certain, desired parts of the nerve tissue, for example. Thus, the optical radiation may be used to affect a specific physiological condition, such as the SAD, for example. In this case there may a plurality of first signal conveyers, such as a plurality of wires, one for each optical radiation source, wherein the plurality of wires provide control and/or power for the optical radiation sources.

Figure 3:
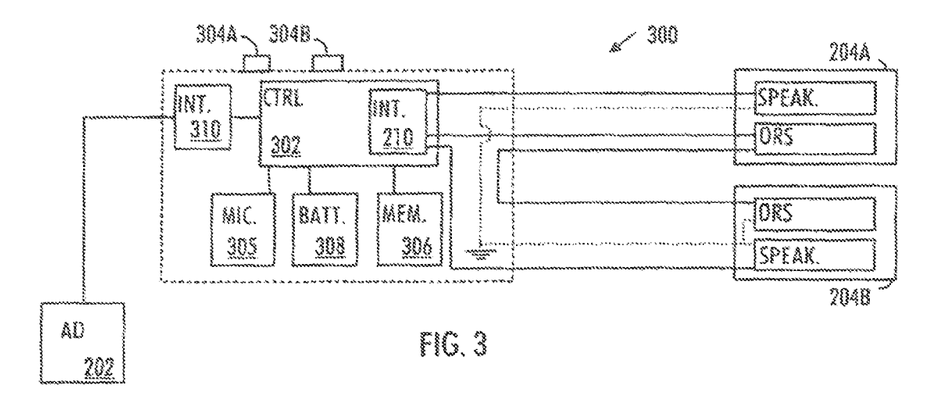
FIG. 3 shows an accessory according to an embodiment.

In an embodiment, the accessory may further comprise a controller 302 operatively coupled to the communication interface 210. This type of accessory 300 is shown in FIG. 3. FIG. 3 shows only the elements and functional entities required for understanding the accessory 300 according to an embodiment. Other components have been omitted for reasons of simplicity. The implementation of the elements and functional entities may vary from that shown in FIG. 3. The connections shown in FIG. 3 are logical connections, and the actual physical connections may be different. The connections can be direct or indirect and there can merely be a functional relationship between components. It is apparent to a person skilled in the art that the accessory 300 may also comprise other functions and structures.

The controller 302 may be implemented with a separate digital signal processor provided with suitable software embedded on a computer readable medium, or with a separate logic circuit, such as an application specific integrated circuit (ASIC). The controller 302 may be, for example, a dual-core processor or a multiple-core processor. The accessory 300 may comprise a memory 306 connected to the controller 302. However, memory may also be integrated to the controller 302 and, thus, no memory 306 may be required. Memory may be used to store information related to the optical treatment that is inputted by the user 102, for example.

The accessory 300 may further comprise a power source 308. The power source 308 may provide power to the accessory 300 in order for the accessory 300 to perform its functionalities. However, the accessory 300 may receive power required for the operation from the audio device 202 connected to the accessory 300. In this case, no separate power source 308 is needed.

The controller 302 may be configured to forward the electrical audio signal received from the audio device 202 to the communication interface 210. This way the communication interface 210 may, as explained in connection with FIGS. 2A and 2B, feed the electrical audio signal to the earpiece unit 204A, 204B. However, in this embodiment, the audio device 202 need not provide the electrical optic signal for the at least one optical radiation source located in the earpiece units 204A, 204B. In stead, the controller 302 may generate and provide the at least one electrical optic signal for driving the at least one optical radiation source to the communication interface 210. By driving it is meant that the at least one optical radiation source is controlled and powered by the provided electrical optic signal. Therefore, basically any electronic device capable of providing the electrical audio signal is, without any functional modification, suitable as the audio device 202. This is because the functionalities needed for generating the user communication interface for controlling the optical radiation and for generating the electrical optic signal are integrated in the controller 302 of the accessory 300, not in the audio device 202. Let us discuss the requirements of the audio device 202 later.

Even though FIG. 3 shows one electrical optic signal and one electrical audio signal for each earpiece unit 204A, 204B, there may be a plurality of electrical optic signals and electrical audio signals conveyed to the earpiece unit 204A, 204B. In this case there may also be a plurality of first and second signal conveyers 208A, 208B, 214A, 214B present between the controller 302 and each earpiece unit 204A, 204B. This is especially advantageous if separate control for the plurality of optical radiation sources 212A, 212B is needed for one earpiece unit. For example, the intensity and/or duration of the optical radiation from each optical radiation source 212A, 212B may be separately controlled.

In the embodiment of FIG. 3, the accessory further comprises an input interface 304A, 304B operatively coupled to the controller 302 and configured allow input commands to be given to the controller 302 by the user 102, wherein the input commands control the magnitude and duration of the at least one electrical optic signal driving the at least one optical radiation source. The user 102 may activate the optical treatment by using the input interface 304A, 304B, for example. The input interface may comprise buttons, a keyboard, means for receiving voice commands, such as microphone 305, touch buttons, slide buttons, etc. As explained earlier, the duration of the electrical optic signal may determine temporal parameters of the optical treatment, such as how long and when the at least one optical radiation source emits optical radiation. The magnitude of the electrical optic signal may determine the intensity of the optical radiation. The magnitude may denote the voltage or current of the conveyed electrical optic signal.

The accessory 300 may, in an embodiment, comprise a second communication interface 310 operatively coupled to the controller 302 and configured to enable communication between the audio device 202 and the controller 302. This may be needed in order to receive the electrical audio signal from the audio device 202 and/or when the accessory 200, 300 is connected to the audio device 202, the audio device 202 may need to obtain identification information from the accessory 200, 300.

Figure 4A:
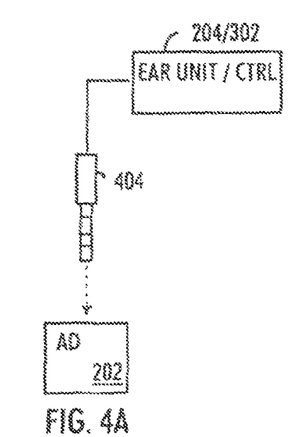
FIGS. 4A, 4B and 4C illustrate exemplary interfaces.
Figure 4B:
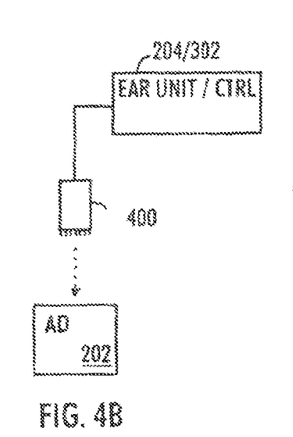
Figure 4C:
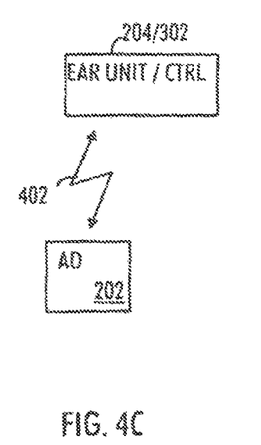

The communication interface, either the communication interface 210 or the communication interface 310, may comprise a universal serial bus (USB) connector, a Bluetooth connection, or an audio jack, for example. These exemplary types of communication interfaces are shown in FIGS. 4A, 4B and 4C. In FIG. 4A, the communication interface 210/310 comprises an audio jack 404, similar to what has already been discussed regarding FIG. 2B. That is, the communication interface 310 may also be an audio jack. In FIG. 4B, the communication interface 210/310 comprises the USB connector 400. In an embodiment of FIG. 4C, the communication interface 210/310 comprises a wireless Bluetooth connection 402 to the audio device 202. This allows a plurality of control signals to be exchanged between the audio device 202 and the earpiece 204 or between the audio device and the controller 302 (to be explained later), thus enabling individual control signals for each of the optical radiation sources.

In the case of wireless Bluetooth connection serving as the communication interface 210 of FIGS. 2A and 2B, each earpiece unit 204A, 204B may comprise a power source providing power for the audio transducers 206A, 206B and for the at least one optical radiation source 212A, 212B. In this example, the first and second signal conveyers may be seen to be comprised in the air interface between the ear piece unit 204A, 204B and the audio device 202 or between the ear piece unit 204A, 204B and the controller 302.

In the case of wireless Bluetooth connection serving as the communication interface 310 of FIG. 3, the power source 308 is needed for providing power for the audio transducers 206A, 206B and for the at least one at least one optical radiation source 212A, 212B.

In the case of wired connection, such as the audio jack 404 or the USB connector 400, serving as the communication interface 210 or 310, the power source providing power for the audio transducers 206A, 206B and for the at least one optical radiation source 212A, 212B may be located in the audio device 202. Thus, the accessory 200 or 300 need not necessarily comprise any power source.

In an embodiment, the controller 302 is in the earpiece unit 204A, 204B. In this case, the controller 302 may control each of the optical radiation sources within the corresponding earpiece unit 204A, 204B separately. This embodiment also provides highly integrated structure because the controller 302, the audio transducer and the optical radiation source(s) are all in one entity connected with a Bluetooth, with a USB, or with an audio jack to the audio device. In this embodiment the earpiece unit comprising the controller 302 may also comprise the battery 308 and/or the microphone 305. The microphone may also be used to receive external audio signals which are then heard by the user via the audio transducers, as described earlier.

Figure 5:
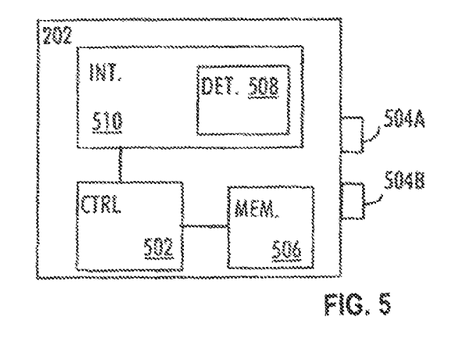
FIG. 5 illustrates an audio device according to an embodiment.

There is also provided the audio device (AD) 202 capable of providing the electrical audio signal. An exemplary audio device 202 is shown in FIG. 5. FIG. 5 shows only the elements and functional entities required for understanding the audio device 202 according to an embodiment. Other components have been omitted for reasons of simplicity. The implementation of the elements and functional entities may vary from that shown in FIG. 5. The connections shown in FIG. 5 are logical connections, and the actual physical connections may be different. The connections can be direct or indirect and there can merely be a functional relationship between components. It is apparent to a person skilled in the art that the audio device 202 may also comprise other functions and structures.

The audio device 202 may comprise, as shown in FIG. 5, a controller 502 configured to generate the electrical audio signal. The controller 502 may be implemented with a separate digital signal processor provided with suitable software embedded on a computer readable medium, or with a separate logic circuit, such as an application specific integrated circuit (ASIC). The controller 502 may be, for example, a dual-core processor or a multiple-core processor. The audio device 202 may comprise a memory 506 connected to the controller 502. However, memory may also be integrated to the controller 502 and, thus, no memory 506 may be required. The memory 506 may be used to store audio tracks, information about the optical treatment as inputted by the user 102, for example. The audio device 202 may further comprise a power source, although not shown in FIG. 5. The power source may be used to provide power to the audio device 202 and also to the accessory 200/300, if needed.

The audio device 202 may further comprise a communication interface 510 configured to output the electrical audio signal. The communication interface 510 is further configured to be coupled to the accessory 200/300. More specifically, the communication interface 510 may be designed to receive the communication interface 210/310 of the accessory 200/300. Thus, the communication interface 510 outputs the signal to the accessory 200/300 so that the accessory 200/300 receives the electrical audio signal driving the audio transducer located in the earpiece units 204A, 204B.

The controller 502 may further generate the at least one electrical optic signal for driving the at least one optical radiation source 212A, 212B of the accessory 200. Consequently, the communication interface 510 may output the electrical optic signal driving the at least one optical radiation source 212A, 212B to the accessory 200. This way, the accessory 200 obtains the electrical optic signal for driving (controlling and powering) the at least one optical radiation source 212A, 212B.

It is to be noted that in the accessory embodiment as shown in FIG. 3, the accessory 300 comprises the controller 302 generating the electrical optic signal driving the optical treatment. In this case the audio device needs to output only the electrical audio signal, not the electrical optic signal. Thus, it behaves like any audio device 202 capable of providing the audio signal, such as a mobile phone.

However, when the accessory does not itself comprise the controller 302, as is the case with the simple apparatus 200 shown in FIGS. 2A and 2B, the audio device 202 may need to generate the electrical optic signal driving the at least one optical radiation source 212A, 212B. In order to do this, the audio device 202 may detect and control the parameters of the at least one optical radiation source 212A, 212B of the accessory 200/300. For example, when the optical radiation source comprises a light emitting diode (LED), the audio device 202 may need to detect the type(s) of the LED(s) in order to know the tuning parameters of the LED(s). Exemplary tuning parameters comprise the resistance of the LEDs, the wavelength of the radiation emitted by the LED, etc. The tuning parameters are important so that optimal power by the electrical optic signal can be fed to the at least one optical radiation source 212A, 212B. When there are different types of LEDs present, the selection of the parameters, such as the magnitude, of the electrical control signal may be based on the LED that is has the highest tuning parameters. Alternatively, each optical radiation source 212A, 212B may be fed separately, as discussed earlier.

The communication interface 510 receiving the communication interface 210/310 of the accessory 200/300 may be equipped with a detecting circuitry 508 configured to detect the accessory 200/300 being coupled to the communication interface 510 of the audio device 202. This way the audio device 202 may know, whether it needs to output both the electrical audio signal and the electrical optic signal for driving the at least one optical radiation source, or only the electrical audio signal. The detection may take place by receiving identification information from the accessory 200/300. This identification information may reveal that the accessory 200/300 requires the electrical audio signal and the electrical optic signal controlling the at least one optical radiation source 212A, 212B to be fed simultaneously.

The audio device 202 may further comprise an input interface 504A, 504B. The controller 502 may thus control the magnitude and duration of the outputted at least one electrical optic signal on the basis of input commands received from the user 102 via the input interface 504A, 504B. The controlling may take place in a similar fashion as with the input interface 304A, 304B regarding FIG. 3.

In an embodiment, the communication interface 510 is an audio plug. The audio plug may be suitable to be coupled with the audio jack 218 of FIG. 2B. Then the controller 502 may apply the microphone input contact of the audio plug as the output of the electrical optic signal for driving the at least one optical radiation source of the accessory 200. This way, the accessory 200 receives the electrical optic signal via the "MIC" contact of the audio jack 218, as explained earlier with regards to FIG. 2B.

Further, the controller 502 of the audio device 200 may switch between using the microphone input contact as the output of the electrical optic signal and as the microphone input. This way, when the electrical optic signal applied in controlling the optical treatment is not being outputted, the contact may be used as the microphone input. This allows dynamic switch in the use of "MIC" contact enabling the audio device 202 to receive audio information even when the audio device is capable of feeding the electrical optic signal controlling the optical treatment.

In an embodiment, the accessory 200, 300 comprises the earpiece unit 204A, 204B, as shown in FIGS. 2 and 3. Let us now discuss further about the earpiece units with reference to three exemplary earpiece units 600, 700 and 800, presented in FIGS. 6, 7 and 8, respectively. These exemplary earpiece units 600, 700, 800 may take the place of the earpiece units 204A, 204B in the accessory 200, 300, if required.

Figures 6A, 6B, 7A, 7B:
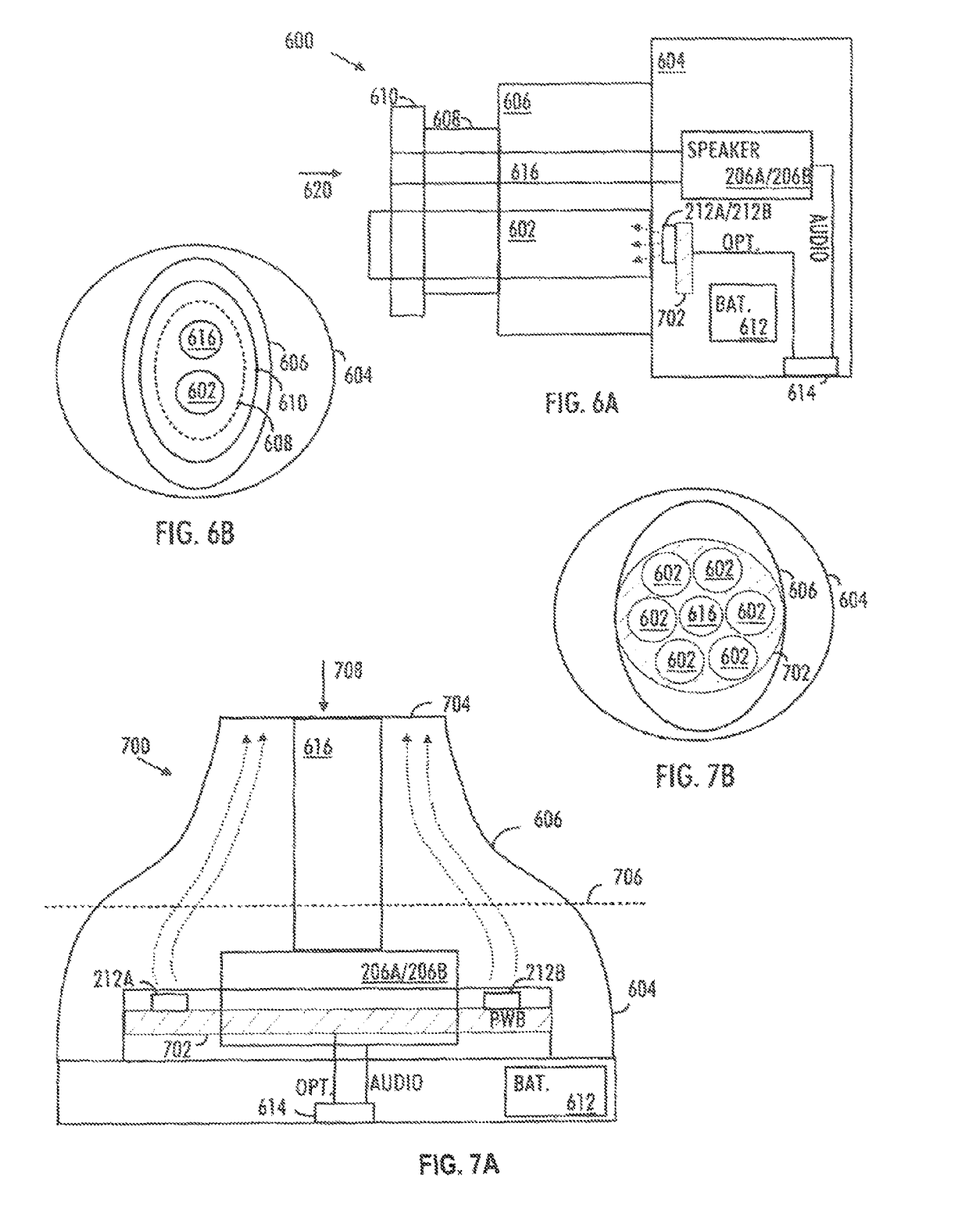
FIGS. 6A and 6B disclose an earpiece unit according to an embodiment.
FIGS. 7A and 7B disclose an earpiece unit according to another embodiment.

In an embodiment, as shown in FIGS. 6A and 6B, the earpiece unit 600 comprises the audio transducer 206A, 206B configured to receive the electrical audio signal ("AUDIO") from a signal reception point 614 and to convert the received electrical audio signal into sound. The earpiece unit 600 further comprises an electric circuit 702 configured to receive the at least one electrical optic signal ("OPT") from the signal reception point 614. The electric circuit may be a printed circuit board, a printed wiring board, an integrated circuit, an organic electric circuit, etc. The earpiece unit 600 may further comprise the at least one optical radiation source 212A, 212B configured to generate optical radiation on the basis of the received at least one electrical optic signal, wherein the generated optical radiation is directed to the ear canal 110A, 110B of the user 102, as shown with dotted lines in FIG. 6A. The light source may be a LED, for example. The electric signals "AUDIO" and "OPT" received may provide power to the speaker 206A, 206B and to the optical radiation source 212A, 212B, respectively. The electrical optic signal may control the optical radiation such that when electric optic signal is received, the optical radiation source 212A, 212B emits optical radiation. The strength (voltage/current) of the electric optic signal may determine the intensity of the optical radiation. The stronger electric optic signal, the higher is the intensity of the optical radiation, defined in luxes, for example. The optical radiation is directed to the ear canal 110A, 110B of the user 102, thus the optical radiation source 212A, 212B does not emit optical radiation to other directions except the ear canal 110A, 110B.

The earpiece units 600 and 700 in FIGS. 6 and 7 may comprise a main body part 604 comprising the audio transducer 206A, 206B and the at least one optical radiation source 212A, 212B. The main body part does not enter into the ear canal 110A, 110B of the user 102. This advantageous because then the audio transducer 206A, 206B and the radiation source 212A, 212B do not generate heat to the ear canal 110A, 110B. Rather, the surrounding air may cool the main body part 604.

The earpiece unit 600, 700 may also comprise a tip part 606 attached to the main body part 604 and configured to fit to the ear canal 110A, 110B of the user 102, wherein the tip part 604 has an elliptical cross section. In FIG. 7, the earpiece unit 700 has been virtually divided by a dashed line 706 into the main body part 604 and the tip part 606. The elliptical cross section of the tip part 604 is shown in more details in FIG. 6B which is the view of the earpiece unit 600 from the direction shown with arrow 620. In the Figure, the main body part 604 has a circular cross section and the tip part 604 has the shape of the largest ellipse in FIG. 6B. Naturally, the shape of the main body part 604 is not limited to circular but basically any shape is suitable. Further, FIGS. 6A and 6B shows that the tip part 606 may comprise a groove 608 and enlargement 610 for enabling tight, yet soft ear fitting. The tight fitting may be obtained by having the at least part of the tip part 606 made of soft, adaptable material such as rubber or foam, for example. The elliptic cross section also aids in providing a tight fit to the ear canal 110A, 110B, because human ear canal 110A, 110B typically has somewhat elliptical cross section. It is also possible to have individually shaped tip portion 604 in order to fulfill the needs of certain users who want their earpiece unit to be designed for his/her ear.

In an embodiment, the earpiece unit 600 comprises at least one light guide 602 configured to direct the generated optical radiation to the ear canal 110A, 110B of the user 102. The light guide 602 may be an optical fiber, for example. The inner surface may be of reflective material so that the light travelling inside the light guide reflects from the inner surface of the light guide 602. Each optical radiation source 212A, 212B may have each own optical guide 602, or one guide 602 may direct radiation from multiple radiation sources 212A, 212B.

In an embodiment, the light guide 602 may be separated from the optical radiation source 212A, 21B, as shown in FIG. 6A. Alternatively, the light guide 602 may be integrated to the optical radiation source. However, the separation is beneficial in order for the heat generated by the optical radiation source 212A, 212B to have sufficient space to dissipate rather than enter the light guide 602. This way, the heat experienced by the ear canal 110A, 110 may be decreased. Moreover, the separation creates an air interface between the optical radiation source 212A, 212B and the light guide 602. The air interface allows the radiation to emit from the radiation source 212A, 212B without distortions. If the light guide 602 were attached to the optical source 212A, 212B, the means for attaching the source 212A, 212B to the guide 602 might distort the emission of the optical radiation. The means for attaching may comprise glue, for example. This might cause some of the emitted optical radiation not to enter the light guide 692 at all but rather to scatter and/or get absorbed in the means for attaching the light guide 602. Further, the separation may ensure that the radiation emitted from the optical radiation source 212A, 212B is optimally directed to the light guide 602. This, however, depends on the applied wavelength of the optical radiation. When the separation is increased, the longer wavelengths do not enter the light guide whereas shorter wavelengths do enter. The correct separation for certain optical radiation may be predetermined by routine testing. Thus, the separation may also be used for filtering out certain wavelengths, if needed.

The at least one light guide 602 may extend from the main body part 604 to inside the tip part 606. That is, the optical fiber, for example, may extend to the part of the earpiece unit 600 that enters the ear canal 110A, 110B of the user 102. This is advantageous so that the radiation may be more efficiently directed to the nerve tissue 104 of the user 102.

The earpiece unit 600 may further comprise a sound guide 616 directing sound to the ear canal 110A, 110B of the user 102, wherein the sound guide 616 extends from the main body part 604 to inside the tip part 606. The extension of the sound guide 616 allows for efficient transfer of the sound generated by the audio transducer 206A, 206B to the ear auditory canal 110A, 110B of the user. Thus, sound may not be allowed to radiate omni-directionally but the sound guide gathers the generated sound and directs the sound into the ear canal 110A, 110B of the user 102. The sound guide 616 may be a separate guide from the at least one light guide 602. This is beneficial, because then both the optical radiation and the sound may be optimally directed for their own specific purposes.

The sound guide 616 and the light guide 602 may have a circular cross-section as shown in FIG. 6B. This is advantageous in order for the tip part 606 to have an elliptic cross section. When two tubes (as exemplary shape of the sound guide 606 and the light guide 602) having circular cross sections, are put next to each other, the surrounding area may have an elliptic cross section, which, as said earlier, is beneficial for tight ear fitting.

In the earpiece unit 700 of FIG. 7, the electric circuit 702, to which the at least one optical radiation source 212A, 212B is mounted on, is a printed wiring board (PWB), wherein the PWB has an aperture allowing the audio transducer 206A, 206B or the sound guide 616 to extend through the PWB 702. This allows very efficient space utilization. By having the sound guide 616 penetrating the hole (aperture) of the PWB 702, the sound guide 616 need not be put next to the PWB 702.

In an embodiment, at least two optical radiation sources 212A and 212B are arranged in the periphery of a circle on the electric circuit 702. Thus, the radiation sources 212A and 212B may surround the sound guide 616 and/or the audio transducer 206A, 206B protruding the PWB 702. This is beneficial in order to save the physical space required by the earpiece unit 700. When there are more than one optical radiation sources 212A, 212B, the directivity of the optical radiation may be controlled by controlling each optical radiation source 212A, 212B with separate electric optic signal, as explained earlier.

In an embodiment, the tip part 606 and the sound guide 616 of the earpiece unit 700 are configured to guide the optical radiation to the ear canal 110A, 110B of the user 102, wherein the inner surface of the tip part 606 and the outer surface of the sound guide 616 are at least partly coated with reflective material. In this embodiment, no additional light guides are needed. When the optical radiation emitted from the at least one optical radiation source 212A, 212B and hits the inner surface of the tip part 606 and/or the outer surface of the sound guide 616, the radiation is reflected back from the hit-point towards the aperture 704. In practice, the tip part 606 and the sound guide 616 serve as the light guide, as shown in FIG. 7A, where the optical radiation, shown as dotted lines, is directed by the tip part 606 and the sound guide 616 to the aperture 704 facing the ear canal 110A, 110B. This is advantageous in order to save the required physical space of the earpiece unit and to save the costs in the manufacturing.

In another embodiment, not shown in FIG. 7A, each optical radiation source 212A, 212B of FIG. 7 has each own optical light guide 602 directing the light from the optical radiation source 212A, 212B to the ear canal 110A, 110B. In this embodiment, the tip part 606 need not be reflective material.

In an embodiment, when the ear piece unit 600, 700 is connected to the accessory 200, 300 via a wireless Bluetooth connection, the earpiece unit 600, 700 may comprise a power source for powering the audio transducer 206A, 206B and the at least one optical radiation source 212A, 212B. When the connection to the accessory 200, 300 is wired, the required operating power may be conducted from the accessory 300 or from the audio device 202, and no additional power source 612 is needed.

FIG. 7B shows the earpiece unit 700 from the side that faces the ear canal 110A, 110B of the user 102, that is, from the direction as shown with an arrow 708 in FIG. 7A. In this example the main body part 604 is of circular cross section. However, any shape of the main body part 604 is possible, for example a rectangular cross section. FIG. 7B also shows the elliptic tip part 604 allowing good ear fitting. The electric circuit 702 is shown with right leaning diagonal lines. The aperture in the electric circuit 702 allows the sound guide 616 to extend through the electric circuit 702 to inside the tip part 606. As explained, in an embodiment, the tip part 606 and the sound port 616 direct the optical radiation from the optical radiation sources 212 to the ear canal 110A, 110B. In another embodiment, the light guides 602 direct the optical radiation, as shown in FIG. 7B.

Figure 8:
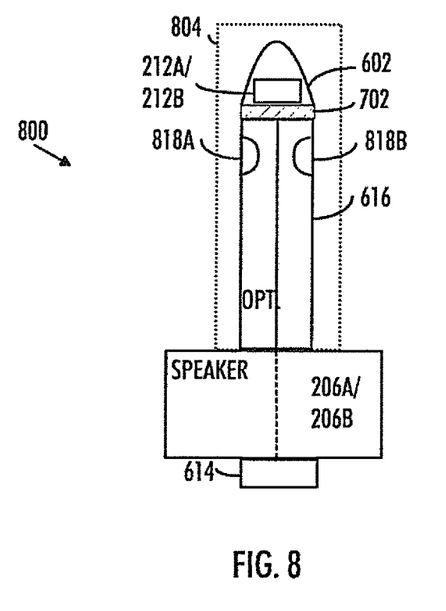
FIG. 8 discloses an earpiece unit according to another embodiment.

FIG. 8 shows a further exemplary embodiment of the earpiece unit. According to an embodiment, the earpiece unit 800 comprises the sound guide 616 directing sound to the ear canal 110A, 110B of the user (102) and the at least one light guide 602 configured to direct the generated optical radiation to the ear canal 110A, 110B of the user 102. In this embodiment, the sound guide 616, the at least one light guide 602, the electric circuit 702 and the at least one optical radiation source 212A, 212B are integrated into one entity 804. The entity 804 is replaceably connected to the rest of the earpiece unit 800. This is advantageous because then the user 102 may change the entity 804 when it wears off in use.

At least part of the entity 804 is, in use, configured to enter the ear canal 110A, 110B of the user 102. Thus, by having the possibility to replace the original entity with another entity, the user 102 may select a suitable entity 804 according to the size of the users 102 ear canals 110A, 110B. For example, if the user 102 has relatively narrow ear canals 110A, 110B, the user 102 may select such an entity 804 which has relatively small diameter or cross-section dimension.

The sound guide 616 of the earpiece unit 800 may comprise at least one aperture 818A, 818B on the longitudinal side of the sound guide 616 for outputting the sound. The electric circuit 702, on which the at least one optical radiation source 212A, 212B is mounted, may locate on the end of the sound guide 616. This structure enables efficient space consumption as the sound guide 616 serves as the mounting plate of the electric circuit 702, on which the at least one optical radiation source 212A, 212B is mounted.

The embodiment as shown in FIG. 8 enables the use of traditional type of earplugs as a starting point for the manufacture of the earpiece 800. The user 102 may then add the entity 804 to the traditional earplug in order to obtain an earpiece unit suitable for optical treatment and audio listening. In order to connect the entity 804 to the speaker 206A/206B, the entity 804 may comprise connection mechanism such as fastening brackets, suspension straps, fixing jaws, etc. In an embodiment, the entity 804 comprises a flexible cover sheet which is extended to cover also the speaker 206A/206B and thus keeps the entity 804 attached to the speaker 206A, 206B.

There is also provided an arrangement for providing audio-optical treatment, wherein the arrangement comprises the audio device 202, the accessory 200, 300, wherein the at least one earpiece unit 204A, 204B is the earpiece unit 600, 700.

Embodiments of the invention may be implemented as computer programs in the audio device 202 or in the accessory 300 according to the embodiments of the invention. There is provided a computer program product embodied on a distribution medium readable by a computer and comprising program instructions which, when loaded into the controller 502 of the audio device 202, configure the controller 502 of the audio device 202 to generate at least one electrical optic signal for driving at least one optical radiation source of the accessory 200. The computer program implemented in the audio device 202 may carry out, but is not limited to, the tasks related to FIGS. 1 to 5.

There is also provided a computer program product embodied on a distribution medium readable by a computer and comprising program instructions which, when loaded into the controller 302 of the accessory 300, configure the controller 302 of the accessory 300 to generate at least one electrical optic signal for driving at least one optical radiation source of the accessory 200. The computer program implemented in the accessory 300 may carry out, but is not limited to, the tasks related to FIGS. 1, 3 to 5.

The computer program may be stored on a computer program distribution medium readable by a computer or a processor. The computer program medium may be, for example but not limited to, an electric, magnetic, optical, infrared or semiconductor system, device or transmission medium. The computer program medium may include at least one of the following media: a computer readable medium, a program storage medium, a record medium, a computer readable memory, a random access memory, an erasable programmable read-only memory, a computer readable software distribution package, a computer readable signal, a computer readable telecommunications signal, computer readable printed matter, and a computer readable compressed software package.

Even though the invention has been described above with reference to an example according to the accompanying drawings, it is clear that the invention is not restricted thereto but can be modified in several ways within the scope of the appended claims. Further, it is clear to a person skilled in the art that the described embodiments may, but are not required to, be combined with other embodiments in various ways.

The invention claimed is:

1. An accessory for an audio device, the accessory comprising:
   at least one earpiece unit each comprising an audio transducer configured to provide sound to a user;
   first signal conveyer configured to convey an electrical audio signal to each audio transducer in order to drive the audio transducer; and
   a communication interface configured to receive the electrical audio signal from the audio device and to output the electrical audio signal to the first signal conveyer,
   characterized in that
   each earpiece unit further comprises at least one optical radiation source configured to provide optical radiation to the user, and the accessory further comprises:
   second signal conveyer configured to convey at least one electrical optic signal to the at least one optical radiation source, in order to drive the at least one optical radiation source, wherein the second signal conveyer is different from the first signal conveyer; and
   the communication interface is further configured to output the at least one electrical optic signal to the second signal conveyer.

2. The accessory of claim 1, wherein the second signal conveyer is a single conducting wire common to each optical radiation source; and
   the communication interface is further configured to output a single electrical optic signal, such that each optical radiation source obtains the same electrical optic signal.

3. The accessory of claim 1, wherein the accessory further comprises:
   a single reference point common to each audio transducer and each optical radiation source.

4. The accessory of claim 1, wherein the communication interface, is an audio jack with four contacts, wherein:
   one contact is for receiving and outputting the electrical audio signal from the audio device to the first signal conveyer in order to generate a right audio channel;
   one contact is for receiving and outputting the electrical audio signal from the audio device to the first signal conveyer in order to generate a left audio channel;
   one contact is for providing the reference point; and
   one contact is for receiving and outputting the electrical optic signal from the audio device to the second signal conveyer in order to control the at least one optical radiation source.

5. The accessory of claim 1, wherein the communication interface is further configured to output a plurality of electrical optic signals, each electrical optic signal controlling a specific optical radiation source.

6. The accessory of claim 1, wherein the accessory further comprises:
   a controller operatively coupled to the communication interface, wherein the controller is configured to:
   forward the electrical audio signal received from the audio device to the communication interface; and
   generate and provide the at least one electrical optic signal for driving the at least one optical radiation source to the communication interface.

7. The accessory of claim 6, wherein the accessory further comprises:
   input interface operatively coupled to the controller and configured to allow input commands to be given to the controller by the user, wherein the input commands control the magnitude and duration of the at least one electrical optic signal driving the at least one optical radiation source.

8. The accessory of claim 6, wherein the accessory further comprises:
   a second communication interface operatively coupled to the controller and configured to enable communication between the audio device and the controller, wherein the second communication interface is an audio jack, a wireless Bluetooth connection, or a universal serial bus connector.

9. An audio device capable of providing an electrical audio signal, the audio device comprising:
   a controller configured to generate the electrical audio signal; and
   a communication interface configured to output the electrical audio signal,
   characterized in that
   the communication interface is further configured to be coir pled to an accessory;
   the controller is further configured to generate at least one electrical optic signal for driving at least one optical radiation source of the accessory; and
   the communication interface is further configured to output the electrical optic signal to the accessory.

10. The audio device of claim 9, wherein the controller is further configured to control the magnitude and duration of the provided at least one electrical optic signal on the basis of input commands received from the user.

11. The audio device of claim 9, wherein the controller is further configured to detect and control the parameters of the at least one optical radiation source of the accessory.

12. The audio device of claim 9, wherein the communication interface is an audio plug and the controller is further configured to:
   apply the micro hone input contact of the audio plug as the output of electrical optic signal for driving the at least one optical radiation source of the accessory; and
   switch between using the microphone input contact as the output of the electrical optic signal and as the microphone unit.

13. An earpiece unit, comprising:
   an audio transducer configured to receive an electrical audio signal and to convert the received electrical audio signal into sound,
   characterized in that the earpiece unit further comprises:
   an electric circuit configured to receive at least one electrical optic signal; and
   at least one optical radiation source configured to generate optical radiation on the basis of the received at least one electrical optic signal, wherein the generated cal radiation is directed to an ear canal of an user.

14. The earpiece unit of claim 13, wherein the earpiece unit further comprises:
   a main body party comprising the audio transduce and the at least one optical radiation source;
   a tip part attached to the main body part and configured to fit to the ear of the user, wherein the tip part has an elliptical cross section.

15. The earpiece unit of claim 13, wherein the earpiece unit further comprises:

at least one light guide configured to direct the generated optical radiation to the ear canal of the user, wherein the at least one light guide extends from the main body part to inside the tip part.

16. The earpiece unit of claim 14, wherein the earpiece unit further comprises:
a second guide directing sound to the ear canal of the user, wherein the sound guide extends from the main body part to inside the tip part.

17. The earpiece unit of claim 16, wherein the electrical circuit is a printed wiring board to which the at least one optical radiation source is mounted on, wherein the printed wiring board has an aperture allowing the audio transducer or the sound guide to extend through the printed wiring board.

18. The earpiece unit claim 13, wherein the earpiece unit comprises at least two optical radiation sources arranged in the periphery of a circle.

19. The earpiece unit of claim 18, wherein:
each of the at least two optical radiation sources has at least one light guide configured to guide the optical radiation to the ear canal of the user; and
the sound guide extends inside the tip part between the guides.

20. The earpiece unit of claim 18, wherein:
the tip part and the sound guide are configured to guide the optical radiation to the ear canal of the user, wherein the inner surface of the tip part and the outer surface of the sound guide are at least partly coated with reflective material.

21. The earpiece unit of claim 13, wherein the earpiece unit comprises:
a sound guide directing sound to the ear canal of the user; and
at least one light guide configured to direct the generated optical radiation to the ear canal of the user,
wherein the sound guide, the at least one light guide, the electric circuit and the at least one optical radiation source are integrated into one entity, wherein the entity is replaceably connected to the rest of the earpiece unit; and
at least part of the entity is, in use, configured to enter the ear canal of the user.

22. The earpiece unit of claim 21, wherein:
the sound guide comprises at least one aperture on the longitudinal side of the sound guide for the outputting the sound; and
the electric circuit, on which the at least one optical radiation source is mounted, locates on the end of the sound guide.

23. A computer program product embodied on a non-transitory distribution medium readable by a computer and comprising program instructions which, when loaded into the audio device of claim 9, configure the controller of the audio device to provide at least one electrical optic signal for driving at least one optical radiation source.

* * * * *